(12) United States Patent
Garcia Morchon et al.

(10) Patent No.: US 9,538,938 B2
(45) Date of Patent: Jan. 10, 2017

(54) SIGNAL TRANSMISSION THROUGH A MEDIUM

(75) Inventors: Oscar Garcia Morchon, Eubdgiveb (NL); Thomas Falck, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 952 days.

(21) Appl. No.: 13/498,176

(22) PCT Filed: Sep. 29, 2010

(86) PCT No.: PCT/IB2010/054381
§ 371 (c)(1),
(2), (4) Date: Mar. 26, 2012

(87) PCT Pub. No.: WO2011/039708
PCT Pub. Date: Apr. 7, 2011

(65) Prior Publication Data
US 2012/0184877 A1 Jul. 19, 2012

(30) Foreign Application Priority Data
Oct. 2, 2009 (EP) .................................... 09172050

(51) Int. Cl.
*A61B 5/00* (2006.01)
*A61B 5/103* (2006.01)
*A61B 8/00* (2006.01)

(52) U.S. Cl.
CPC .............. *A61B 5/103* (2013.01); *A61B 5/4869* (2013.01); *A61B 8/00* (2013.01); *A61B 5/441* (2013.01); *A61B 5/4504* (2013.01)

(58) Field of Classification Search
CPC ......... A61B 5/103; A61B 8/00; A61B 5/4869; A61B 5/441; A61B 5/4504
(Continued)

(56) References Cited

U.S. PATENT DOCUMENTS

| 4,913,157 A | 4/1990 | Pratt et al. |
| 4,930,511 A | 6/1990 | Rossman et al. |

(Continued)

FOREIGN PATENT DOCUMENTS

| JP | 2001128973 A | 5/2001 |
| JP | 2007016229 A | 1/2007 |

(Continued)

OTHER PUBLICATIONS

L. Zhong, et al., "OsteoConduct: Wireless Body-Area Communication Based on Bone Conduction", Proceed. 2nd. International Conf. on Body Area Networks, Jun. 1, 2007, pp. 108.

*Primary Examiner* — Max Hindenburg
*Assistant Examiner* — Jonathan M Foreman

(57) ABSTRACT

System using on- or in-body communication technologies such as body-sound communication (BSC) or body-coupled communication (BCC) to obtain information on the body composition of a patient (e.g. water content/hydration level on bone density/joint status). The system, in a preferred embodiment, comprises a transmitter, receiver and processor connected to the receiver. The transmitter is arranged to transmit a signal through a medium (the body of the patient), the signal comprising a plurality of different frequency components and transmission technologies. The receiver is arranged to receive the signal following propagation through the said medium. The processor is arranged to generate, at a first time, one or more transfer functions from the received signal, each transfer function defining values for a predetermined signal parameter at different frequencies. The processor then generates, at a second time, one or more further transfer functions from the received signal and compares a transfer function with the further transfer function for the same signal parameter. An output is generated if (Continued)

the difference between the transfer function and the further transfer function exceeds a preset threshold.

15 Claims, 7 Drawing Sheets

(58) Field of Classification Search
USPC .............................. 600/300, 301, 546, 547
See application file for complete search history.

(56) References Cited

U.S. PATENT DOCUMENTS

| | | |
|---|---|---|
| 5,615,689 A | 4/1997 | Kotler |
| 6,443,907 B1 | 9/2002 | Mansy et al. |
| 2002/0156378 A1 | 10/2002 | Sakai |
| 2004/0220492 A1 | 11/2004 | Kodama et al. |
| 2005/0004491 A1 | 1/2005 | Shiokawa et al. |
| 2009/0043222 A1 | 2/2009 | Chetham |
| 2009/0149748 A1 | 6/2009 | Lenhardt et al. |
| 2011/0009747 A1 | 1/2011 | Pukkai |

FOREIGN PATENT DOCUMENTS

| | | |
|---|---|---|
| JP | 2008194240 A | 8/2008 |
| JP | 2008206633 A | 9/2008 |
| JP | 2008284136 A | 11/2008 |
| WO | WO0175766 | 10/2001 |
| WO | WO0176220 | 11/2001 |
| WO | WO0230280 | 4/2002 |
| WO | WO2004006764 | 1/2004 |
| WO | WO2007025218 | 3/2007 |
| WO | WO2007113756 | 10/2007 |
| WO | 2009100491 A1 | 8/2009 |

SIGNAL TRANSMISSION THROUGH A MEDIUM

FIELD OF THE INVENTION

This invention relates to a system for, and to a method of, transmitting a signal through a medium. In one embodiment, the invention can be used as a body composition analyzer.

BACKGROUND TO THE INVENTION

Determining the body composition of an individual is of fundamental importance in many applications within the medical and fitness domains. An individual's personal parameters such as water, muscle or fat percentage play a key role to determine the health state of that individual. For example, determining the amount of water in the human body is especially important in a number of settings to prevent people from becoming dehydrated. However, current systems do not allow for the automatic measurement of the actual water percentage in the body without error, or even with small error. Consequently, this has to be determined or approximated manually. For example, nurses have to physically write down the amount of water a patient drinks and/or measure their urine to try to find out whether or not the patient's water balance is acceptable. This procedure is regularly practised, in intensive care stations, for example. This method is not only cumbersome, but also imprecise since it does not take into account other effects on the patient, such as sweating.

Therefore, having an approach or system that allows for the automatic and precise measurement of the actual composition of an individual's body is of key importance in medical and fitness applications. Some current systems for the analysis of body composition are based on bio-impedance. Bio-impedance (see for example, http://en.wikipedia.org/wiki/bioimpedance) measures the propagation features of an electric current through the human body. The propagation of electricity (electric current) depends on different parameters such as the signal frequency. However, the current systems based on bio-impedance are not precise enough to provide results of sufficient reliability. There exist a number of models to choose from, in order to find out the actual body composition of the patient. Although the choice of the correct model is crucial, it is not always evident, since it depends upon a number of parameters such as the age or gender of the individual being assessed. Additionally, bio-impedance based systems require a number of electrodes interconnected by wires that limits the user experience when designing wearable systems and makes the resulting scheme more complex to use and expensive. Finally, these systems are highly dependent on the user's body position when the measurements are taken. As a result, current systems do not allow for the automatic and precise measurement of the patient's parameters. Furthermore, the systems based on bio-impedance present several drawbacks such as the use of imprecise models or the need of many electrodes.

International Patent Application Publication WO 2007/113756 discloses a method and apparatus for determining hydration levels by measuring velocity change. In accordance with an example embodiment, an apparatus includes a transmitting transducer operative to transmit a mechanical wave. The apparatus also includes a receiving transducer operative to receive the mechanical waves transmitted from the transmitting transducer, wherein the transmitting transducer and the receiving transducer are disposed over a same side of a layer of tissue. The apparatus includes a processor operative to calculate a velocity of the mechanical wave in a medium, wherein the velocity is representative of a hydration level in the medium. While the technology disclosed in this Publication is an improvement over many known techniques, it still nevertheless requires an accurate measurement of distance between the two transducers to be taken, which can be difficult to achieve in many practical situations with a patient, and also requires that a velocity calculation be made of the wave, which can be affected by factors other than just the hydration level such as the pressure of the transducers on the tissue, the temperature, or the orientation of the muscle fibers.

It is therefore an object of the invention to improve upon the known art.

SUMMARY OF THE INVENTION

According to a first aspect of the present invention, there is provided a system comprising a receiver arranged to receive a signal following propagation through a medium, and a processor connected to the receiver and arranged to generate, at a first time, one or more transfer functions from the received signal, the or each transfer function defining values at different frequencies for a predetermined signal parameter, to generate, at a second time, one or more further transfer functions from the received signal, to compare a transfer function with the further transfer function for the same signal parameter, and to generate an output if the difference between the compared transfer function and further transfer function exceeds a preset threshold.

According to a second aspect of the present invention, there is provided a method comprising receiving a signal following propagation through a medium, generating, at a first time, one or more transfer functions from the received signal, the or each transfer function defining values at different frequencies for a predetermined signal parameter, generating, at a second time, one or more further transfer functions from the received signal, comparing a transfer function with the further transfer function for the same signal parameter, and generating an output if the difference between the compared transfer function and further transfer function exceeds a preset threshold.

Owing to the invention, it is possible to provide a system that uses on- or in-body communication technologies such as body-sound communication or body-coupled communication to determine the body composition of a patient. The use of all these technologies in a stand-alone or combined fashion allows overcoming the existing gap and provides a complete system for automatic and precise analysis of the body composition. The proposed system can be used in a number of different applications including monitoring of patients at intensive care units and general wards in hospitals, and elderly people in senior living facilities or at home.

By using transfer functions taken at different times and comparing the different results, it is possible to determine a non-standard reading without having to accurately measure or calculate the distance travelled by the signal or the speed of the signal which greatly increases the usability and effectiveness of the system. In this setting, a set of transducers may be attached to the body without having to be connected via wires to each other. The transducers may work as transmitters or receivers at different times measuring the relative variation of the delay of a sound wave propagated through the body at different times so that it is possible to derive the progressive variation of body components such as water percentage without need for specific knowledge of the relative distances between transducers.

Preferably, the system further comprises a transmitter arranged to transmit the signal through the medium, the signal comprising a plurality of different frequency components. The signal that is received by the receiver can be generated by some background action, such as a user walking which will create sound waves in their legs, for example. In a preferred embodiment, the system includes a transmitter that is used to generate the signal and transmit that signal through the medium.

Advantageously, the system further comprises a transducer arranged to receive the signal following partial propagation through the medium and to transmit a verification signal to the processor, wherein the processor is arranged, when comparing a transfer function with the further transfer function for the same signal parameter, to adapt the comparison according to the verification signal. It is important to ensure that the distance between the transmitter and the receiver does not change over time. In order to compensate for this, a third transducer could be used at a half distance between the transmitter and the receiver for verification purposes. This transducer can provide a verification signal that can be used to compensate for any change in the perceived movement between the transmitter and the receiver.

In a preferred embodiment, the transmitter, receiver and processor are formed in a single device. The system analyses the transmission function between two sensors, a transmitter and a receiver. It is also possible to get some information using with a single sensor operating as both a transmitter and a receiver at the same time. Depending on the patient's body composition, for example, the amount of water, the reflected signal will present different features, higher or lower delay or attenuation at different frequencies in the transmission of a sound wave. Using a single device containing all of the components there is no need to compensate for distance movement between the transmitter and the receiver, as this distance is fixed within the device.

Ideally, the transmitter is arranged to generate the signal using multiple different transmission technologies. In this case, the system will use several different communication technologies including body-coupled communication (BCC), or body-sound communication (BSC) or bio-impedance to improve the actual measurements provided by the use of systems using a single technology such as the current systems based on bio-impedance. Transfer functions would be generated for responses for the different technologies for a number of parameters. Since the number of responses is higher and non-correlated as they are generated from different measurement systems, then it is possible to combine them obtaining a more precise result.

BRIEF DESCRIPTION OF THE DRAWINGS

Embodiments of the present invention will now be described, by way of example only, with reference to the accompanying drawings, in which:—

DETAILED DESCRIPTION OF THE EMBODIMENTS

Figure 1A:
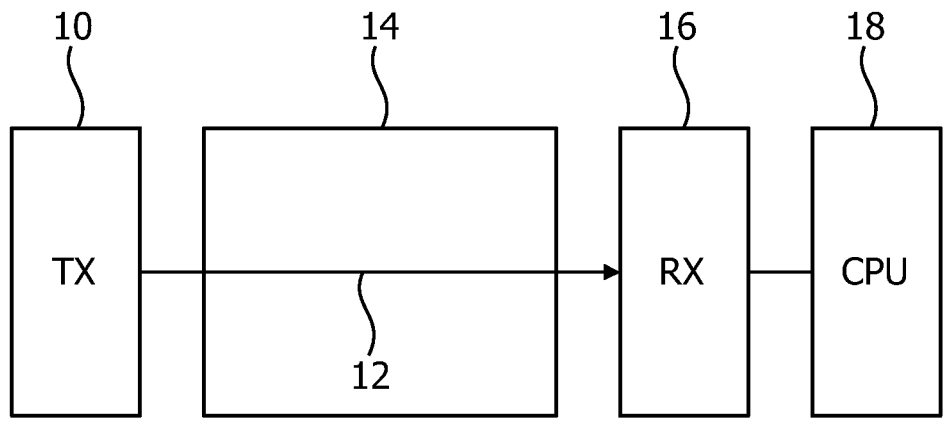
FIG. 1a is a schematic diagram of an embodiment of a system for transmitting a signal through a medium.
Figure 1B:
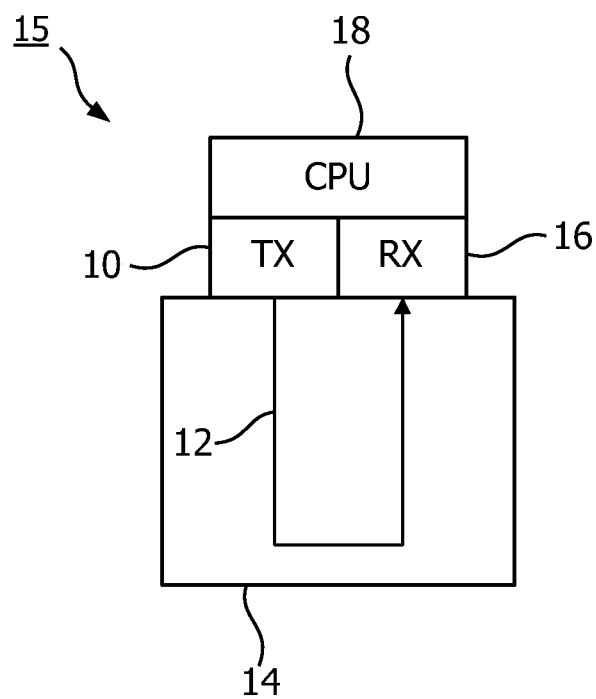
FIG. 1b is a schematic diagram of an alternative embodiment of a system for transmitting a signal through a medium.

FIGS. 1a and 1b show two embodiments of the system, which comprises a transmitter 10 that is arranged to transmit a signal 12 through a medium 14, a receiver 16 arranged to receive the signal 12, following propagation through the medium 14, and a processor 18, which is connected to the receiver 16. The signal 12, which is transmitted through the medium 14, comprises a plurality of different frequency components. These different frequency components may be present within the signal 12 in parallel, or the frequency of the signal 12 may vary over time in order to produce the different frequency components which propagate through the medium 14. The receiver 16 receives the signal 14 after it has passed through the medium 14 and the processor 18 has access to this received signal.

The transmitter 10 and the receiver 16 may be formed as separate devices, as shown in FIG. 1a, with the processor 18 present with the receiver 16. Alternatively, the transmitter 10, receiver 16 and processor 18 may all be formed in the same device 15, as shown in FIG. 1b. The path taken by the signal 12 will depend upon the nature of the medium 14. As discussed above, one application of the systems of FIGS. 1a and 1b is the measurement of one or more body properties of a patient, such as the water content (level of hydration) or the detection of an abnormal level of one or more body properties of the patient. In this case, the medium 14 constitutes at least part of the body of the patient. The transmitter 10 may be attached or in contact with one part of the patient's body, and the receiver 16 may be attached or in contact with a different part of the patient's body.

The processor 18 is arranged to generate, from the signal 12, at a first time, one or more transfer functions, where each transfer function defines values at different frequencies for a predetermined signal parameter. This process is described in more detail below. The processor 18 is then arranged to generate, at a second time, one or more further transfer functions from the received signal. The processor 18 then compares a transfer function (from the first measurement time) with the further transfer function for the same signal parameter (from the second measurement time), and thereby generates an output if the difference between the transfer function and the further transfer function exceeds a preset threshold.

The system uses different body communication technologies to determine the patient's body composition including water, fat, muscle, or bone percentage. The actual, and more specific, contributions of the system are as follows, the use of body-communication technologies such as body-coupled communication (BCC), or body-sound communication (BSC) through the body to determine the body composition. These terms are defined in more detail below. In one embodiment, the combination of a number of body communication technologies such as BCC, BSC or bio-impedance can be used to improve the measurements of the patient's body composition. A differential calculation of the body composition of the patient is used, by detecting small variations of the measurements, thereby comparing measurements made at different times.

Figure 2:
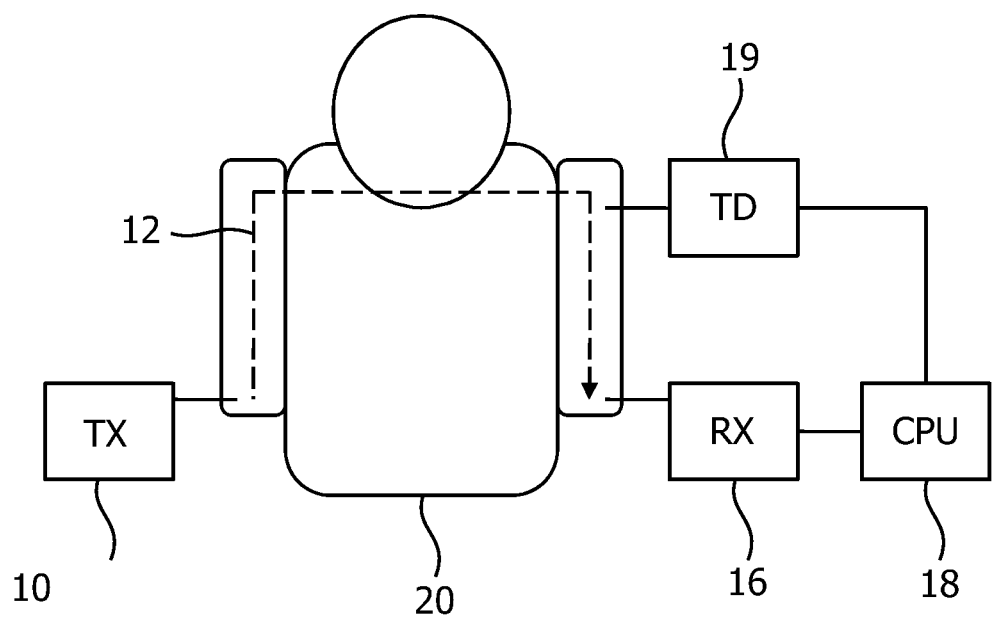
FIG. 2 is a schematic diagram of a patient using the system of FIG. 1.

The system uses body communication technologies to determine the patient's body composition, instead of using bioelectrical impedance analysis. Two possible technologies are body-coupled communication (BCC) and body-sound communication (BSC). BCC refers to the transmission of information on the body by means of the transmitter 10 and the receiver 16 that are capacitively coupled, as shown in FIG. 2. In this context, given that the transmitter 10 and the receiver 16 can be located on the hands of a person 20, the communication goes along the body from the hand with the transmitter 10 to the hand with the receiver 16. Further information can be found in "Body-coupled communication for body sensor networks", for example, available online at http://portal.acm.org/citation.cfm?id=1460273.

BSC refers to the use of the human body as a transmission medium of sound waves of any frequency. In this setting, given the transmitter 10 and the receiver 16, the communication goes through the body that is actually between the transmitter 10 and the receiver 16. Further detail can be found in Lin Zhong, Dania El-Daye, Brett Kaufman, Nick Tobaoda, Tamer Mohamed, Michael Liebschner, "Osteo-Conduct: Wireless Body-Area Communication based on Bone Conduction" In Proc. of BodyNets 2007. In the case of BCC the communication is limited to a few millimeters under the skin due to the specific features of the communication technology. For BSC the communication can go through many different tissues depending on the measurement goals. In an exemplary setting, the communication can go mainly through the bones of the patient 20, since the bones are solid matters that actually transmit much better the sound waves. In this setting, the rest of the human tissue is also involved in the communication. For instance, in the case of BSC, the muscles and fat tissue surrounding the bones absorb a different amount of energy from the sound wave depending on different factors such as frequency. In this setting, the system can be used to measure the amount of water by measuring the variations of specific transfer functions depending on the changes on the water around the bones. This system can also be applied to measure variations in the bone structure caused by injuries or diseases such as osteoporosis.

In a simple approach, it is possible to use a body communication technology, or a combination of technologies including bio-impedance, to determine the body composition of the patient 20. The approach would be as follows, with the system overall requirements of the transmitter 10 and the receiver 16 based on the chosen communication technology. The transmitter 10 transmits the signal 12 to the receiver 16 through or on the body 14 according to a specific protocol. An algorithm is operated by the processor 18, which is used to model and analyze the patient's body composition as a function of different parameters such as frequency or signal amplitude. One or more transfer functions are generated from the received signal 12.

FIG. 2 also shows the use of a transducer 19 which is positioned between the transmitter 10 and the receiver 16, in terms of the path of the signal 12 through the body of the patient 20. The transducer 19 receives the signal 12 following partial propagation through the medium and transmits a verification signal to the processor 18. The processor 18 is arranged, when comparing several transfer functions taken at different times, to adapt the comparison according to the verification signal received from the transducer 19. The transducer 19 is providing a compensation function within the system and data from the transducer 19 can be used to correct measurements taken at the receiver 16 and processor 18 that have been affected by movement of the patient 20, which might result in a change in the path of the signal 12 that passes from the transmitter 10 to the receiver 16.

Figure 3:
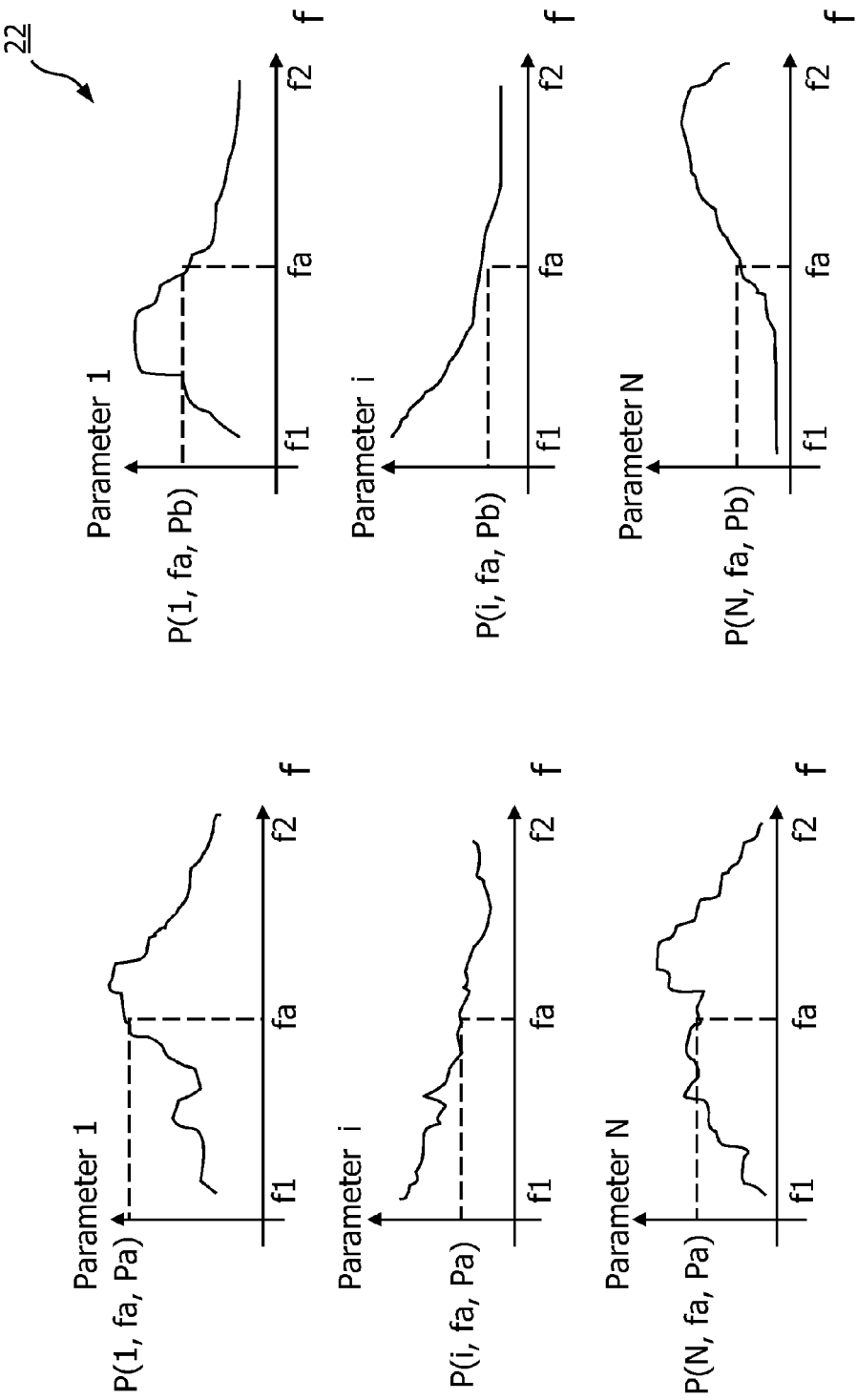
FIG. 3 is a diagram of transfer functions.

In an embodiment of the invention, it may be necessary to perform a calibration phase to allow for the system operation. During the calibration phase the transmitter 10 and receiver 16 are tried on different patients 20 representing different known body composition patterns. In this phase, it is possible to model transfer functions that correspond to the actual patient body composition as a function of different parameters such as frequency, as shown in FIG. 3. The transfer functions 22 measure how the input changes depending on the actual transmission medium 14. This can be determined by different parameters such as group velocity, phase velocity, dispersion, wave velocity, attenuation, delay, and/or wave amplitude, etc. Three transfer functions 22 are shown for two different patients Pa and Pb. Parameters 1 to N can be modeled as functions 22.

In relation to the measured parameters mentioned above, the group velocity of a wave is the velocity with which the variations in the shape of the wave's amplitude (known as the modulation or envelope of the wave) propagate through space, for example, the musculoskeletal system in the case of BSC. The phase velocity (or phase speed) of a wave is the rate at which the phase of the wave propagates in space. This is the speed at which the phase of any one frequency component of the wave travels. Dispersion is the phenomenon that the phase velocity of a wave depends on its frequency. Wave velocity is the speed at which the energy moves through the medium, again, for example, the musculoskeletal system in the case of BSC. Wave amplitude is the amplitude of a wave. Amplitude of transmitted and reflected waves depends on the transmission medium and frequency.

Figure 4:
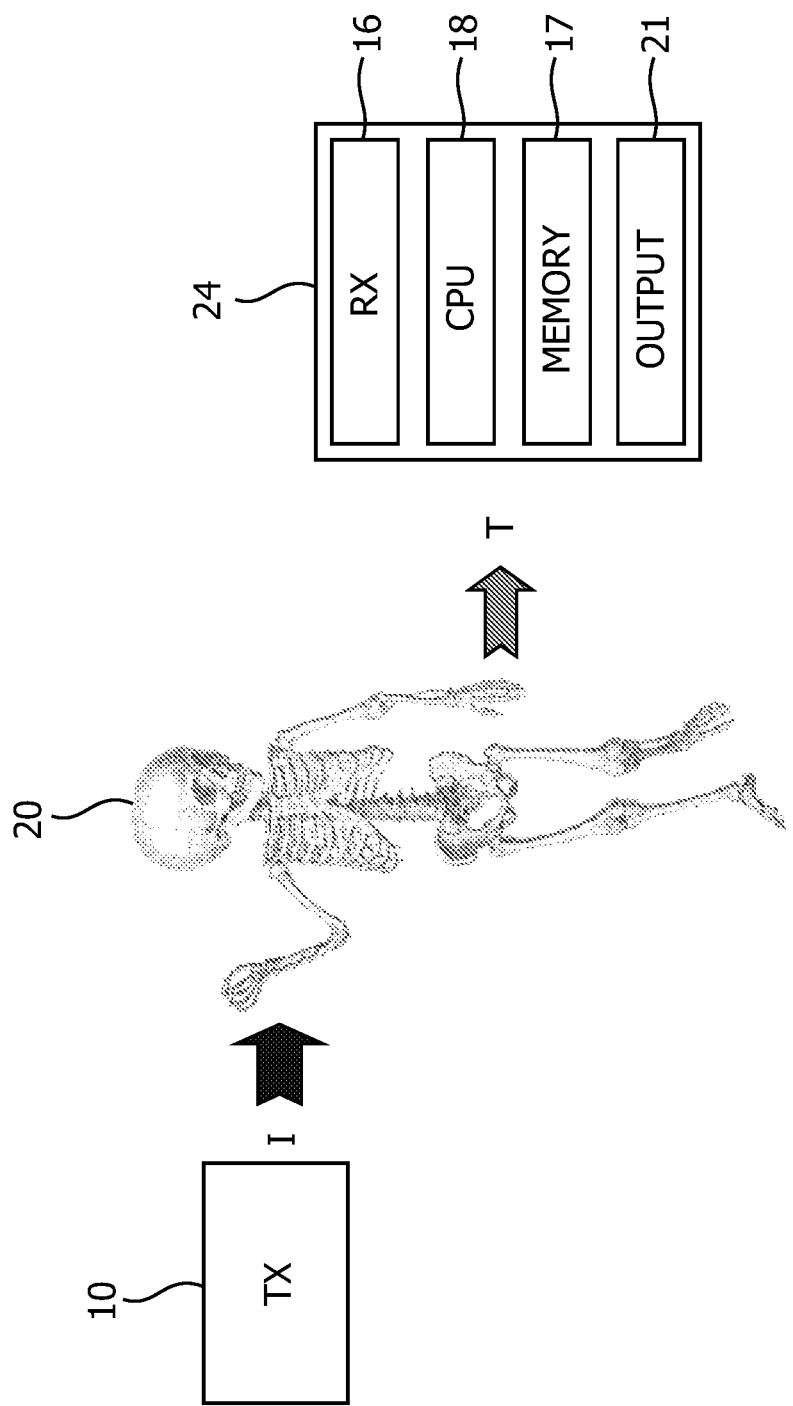
FIG. 4 is a further schematic diagram of the system.

The analysis of the body composition occurs when the body composition of a user 20 needs to be determined. FIG. 4 shows how the user 20 might use the transceiver 10 to transmit a sound wave (in the case of BSC) through the patient's body. The receiving device 24 comprises both the receiver 16 and processor 18, and additionally a memory 17, and would get the information from the received signal and will analyze the response. The memory 17 is required for storing known models that are used by the processor 18 in comparison with the received signal. The device 24 can analyze the received wave and compare it with existing models obtained during a calibration phase. The calibration phase may be specific for that user 20 or may be generalized to users of a similar type, by age and gender etc.

The result of the analysis of the received wave (which is the original signal 12 after it has propagated through the body 10) can be seen as a collection of parameters (as described above: group velocity, phase velocity, dispersion, wave velocity, wave amplitude, etc.) depending on, for example the frequency of the transmitted signal. The transmitted signal 12 might be a sound wave in the case of BSC. The response received by the device 24, which is actually a signature of the body composition of the person 20, is compared against existing models to determine different body parameters such as the water and/or fat percentage of the user 20 or other parameters such as bone composition or early detection of lesions. In this way, the processor 18 will generate transfer functions for the received signal.

The device 24 also comprises an output device 21, which could be an audio device and/or a display device (such as a touchscreen), for example. This output device 21 is designed to provide feedback directly to the user 20 or to a suitably qualified physician. The output device 21 provides an output under the control of the processor 18. The processor 18 is arranged to generate an output if the difference between transfer functions taken at different times exceed a preset threshold. In this way, the device 24 directly monitors the patient 20 and provides real-time measurement, processing and output. In exemplary embodiments, the devices of FIGS. 1 and 2 will also be provided with output devices 21 to provide direct feedback. Alternatively, or in addition, the processor 18 is connected to a short-range wireless transmitter (such as a Bluetooth transceiver) to communicate with a local system such as a desktop computer.

Figure 5:
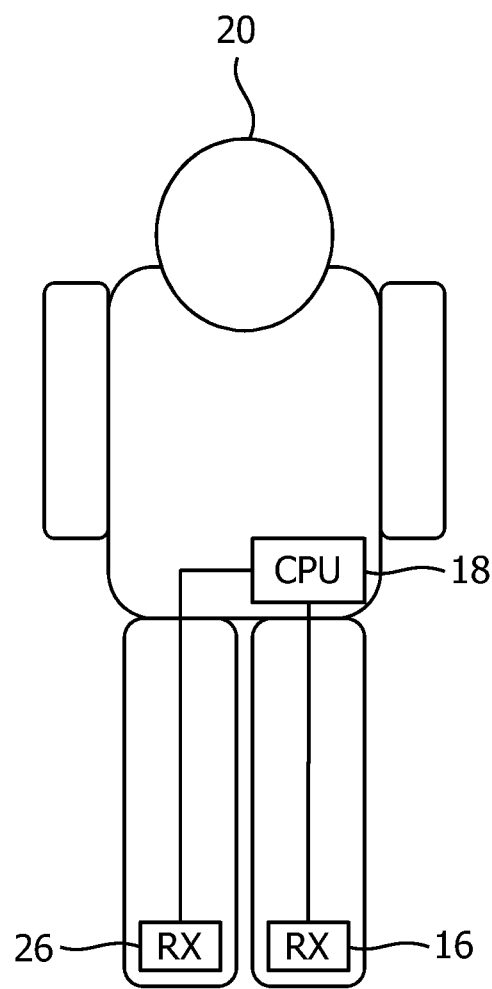
FIG. 5 is a schematic diagram of a further embodiment of the system.

The system can also be configured to work in a silence mode in which the transmitter 10 does not transmit any information, or indeed there is no transmitter 10 present, and only the receiver 16 is operative. This approach is shown in FIG. 5, and can be used to analyze also body composition and prevent injury from lesions, for example. The system further comprises a second receiver 26, which is also arranged to receive a signal following propagation through the medium 20, and is connected to the processor 18. The processor 18 can be arranged to compare the output of the first and second receivers 16 and 26 and generate an output accordingly. The signal 12 is received at a second location and the processor 18 compares the received signals 12 at the different locations and generates an output based on the difference in the signals at the different locations.

For instance, if applied to a scenario in which a person is walking (elderly) or doing sports (for example running), the receivers 16 and 26 can be configured to monitor the sound originated from the steps during the activity. For instance, a change in the frequency might indicate fatigue, or if two receivers 16 and 26 are used (one in each foot), it is possible to distinguish whether the sound coming from one foot is louder, which might indicate a possible lesion. Further, the receivers 16 and 26 might be configured with high sensibility to analyze sounds originated from anomalous sounds originated in joins such as knees. The receiver can also be used to measure the heart rate.

The comparison of the response (or signature) depicted in FIG. 3 illustrates how the receiver 16 receives two different responses or signatures for two different persons 20 with different body compositions. The responses are measured for a number of parameters for a fixed frequency or a range of frequencies, and compared with existing models. The functions 22 shown in FIG. 3 show that the processor 18 will generate one or more functions that represent specific parameters over different frequencies of the received signal. A parameter could be something as simple as wave amplitude, in which the transfer function 22 represents a frequency against amplitude graph for the received signal. This might be parameter 1, for example, in which case the two transfer functions 22 at the top of FIG. 3 represent this function 22 for two specific individuals 20.

It is also possible to use a combined approach that aims at further exploiting the communication features of different technologies. This utilizes the idea that different communication technologies exhibit completely different transfer functions that can be used to model the actual body composition. For example, if using bio-impedance, the system measures the received amount of an electrical signal. This depends on the body tissues and the signal frequency. However, the only thing that is measured is the transmission of the electrical signal. In relation to the transmission of sound through the body, the system is going to be modeled in a completely different way since the system is receiving sound waves instead of electrical signals. From this point of view, the transfer functions of different communication technologies complement each other.

In a preferred embodiment, therefore, the system will use several communication technologies including BCC, BSC or bio-impedance to improve the actual measurements provided by the use of systems using a single technology such as the current systems based on bio-impedance. Transfer functions 22 similar to those shown in FIG. 3, would be generated for responses for the different technologies for a number of parameters. Since the number of responses is higher, the involved technologies are completely different and the total number of parameters is also higher, and therefore the system is able to obtain a more precise result. This can be easily understood, as a model for a specific system might not discern some components of the body (for example, the exact amount of water) for some settings. If there is added an extra transmission technology, then it is possible to improve the final result, since the model of the second technology will measure the body composition in the right way for the specific body feature being determined. For instance, current systems based on bio-impedance can be imprecise as for the same percentage of water in the body, (i) the water can be intra- or inter cellular, and (ii) different concentrations of electrolytes in the body are possible. Therefore, the same water percentage might lead to different bio-impedance results. In this system, it is possible to remove some uncertainty by, for instance, determining the amount of intra- or inter cellular amount of water by means of other technologies, for example body sound communication. Thus, the overall system can be more accurate.

The system also uses differential and progressive measurements. This provides a differential and adaptive analysis of the body composition of the patient 20. This builds on the fact that measuring the actual composition of the patient's body from scratch is difficult since a lot of parameters are involved. However, if it is assumed that the system has access to the actual values of, for example, water percentage $W_T$ at time T, and the measurement value $V_T$ of the body composition analyzer also at time T. At time T+δ it can be observed that the output of the body composition analyzer $V_{T+\delta}$ and use the difference of those two values ($V_T-V_{T+\delta}$) to adapt the water percentage value at time T+δ. For instance, a simple algorithm can calculate this as a function of the difference of those values and the previous water percentage $W_{T+\delta}=f(W_T, (V_T-V_{T+\delta}))$. This approach might be used to measure other parameters. For instance, it might be also applied to measure the way a person walks or the sounds originated from this activity. A time T, the system might sense the sound originated from the steps from the right and left feet. A delta later, the measurement might be repeated analyzing deviations.

Figure 6:
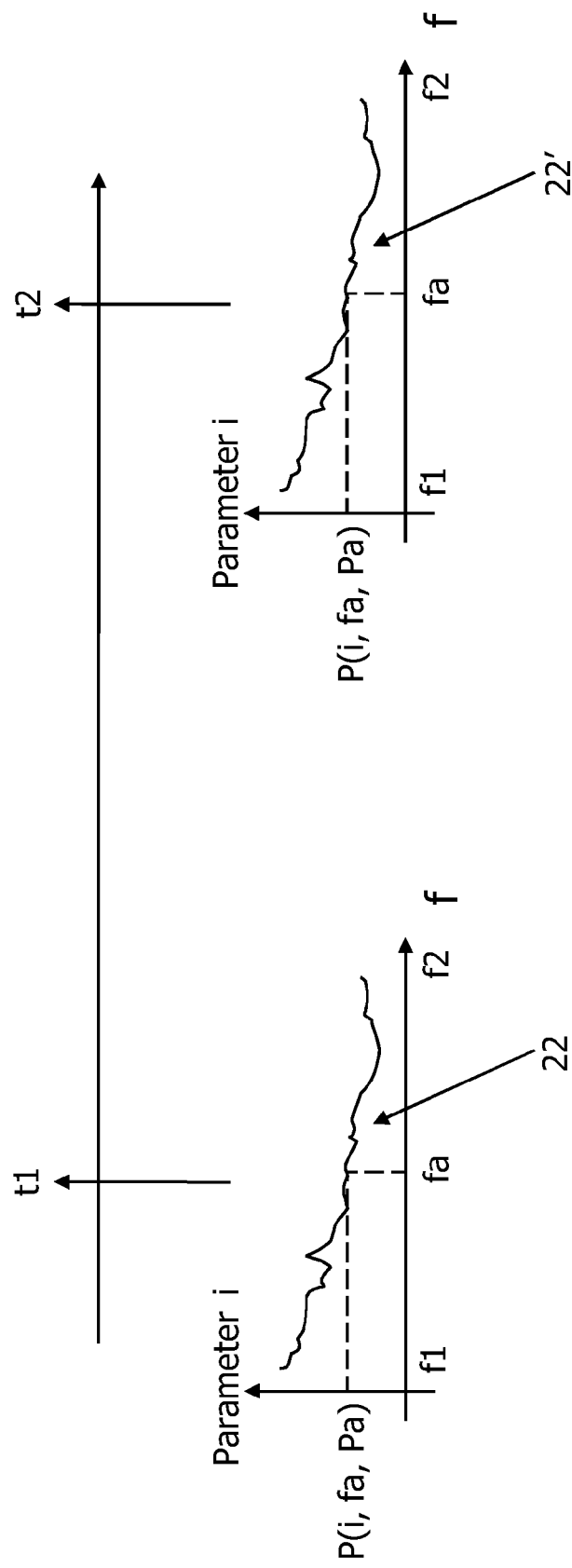
FIG. 6 is a schematic diagram showing different transfer functions obtained at different times.

FIG. 6 illustrates the use of differential measurements. In order to get useful information from sound speed, the system needs to know the distance between the transmitter 10 and the receiver 16. This might not be practical for some systems. In order to overcome this problem the user 20 fixes the transmitter 10 and receiver 16 on their body. A measurement at a first time t1 represents the normal situation. A reference delay for sound communication can also be measured. Every x seconds, the system measures again the delay between the transmitter 10 and the receiver 16. Higher delay means, lower sound speed, and thus, higher water content. In this way, it is possible to plot the trend. At a second time t2 a further transfer function 22' is measured. It is important to maintain that the transducer distance does not change over time. For example, as shown in FIG. 2, a third transducer 19 could be used at a half distance between the transmitter 10 and the receiver 16 for verification purposes. Hydration status should influence delay time from this transducer to others in the same direction, but movement of the transmitter 10 and the receiver 16 would affect only one of the delays or both delays in opposite direction.

Figure 7:
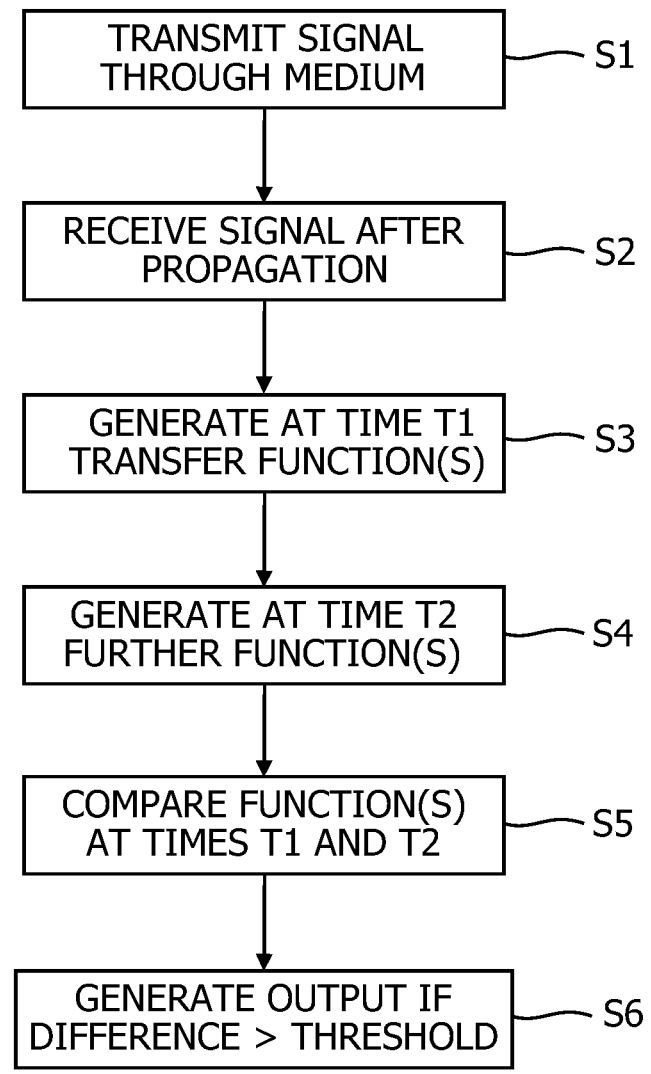
FIG. 7 is a flowchart of a method of operating the system.

The preferred method of operating the system is summarized in FIG. 7. The method comprises, step S1 transmitting the signal 12 through the medium 14, the signal 12 comprising a plurality of different frequency components and step S2 receiving the signal 12, following propagation through the medium 14. At the receiving end of the system there is then carried out the step S3 of generating, at a first time t1, one or more transfer functions 22 from the received signal 12, where each transfer function 22 defines values at different frequencies for a predetermined signal parameter, and also generating, at a second time t2, one or more further transfer functions 22' from the received signal 12. At step S5 there is then carried out the step of comparing a transfer function 22 with the further transfer function 22' for the same signal parameter, and, step S6, generating an output if the difference between the transfer function 22 and the further transfer function 22' exceeds a preset threshold.

The system can be designed in such a way that the transmitter 10 and the receiver 16 form part of a single device 15, such as a bracelet, where the distance between the transmitter 10 and the receiver 16 is adjustable (but always unknown) at an initial time. After fitting the bracelet to, the wrist of the user 20, the transmitter 10 sends a wave sound pulse to the receiver 16. Both the transmitter 10 and receiver 16 analyze the trend therefore of the water variation based on the delay variations.

The system can be further enhanced by providing synchronization between the transmitter 10 and the receiver 16, so that the delay between the transmitted and received sound waves can be measured with precision. This can be done by simply using a wire joining the transmitter 10 and receiver 16. Alternatively, the transmitter 10 and receiver 16 might also include a wireless interface and a clock synchronization protocol that allows synchronizing the CPU clocks of both components.

In some relevant applications, the described system can operate with a multitude of transmitters and receivers located on different parts of the patient's body. This can allow the system to measure (relative variations of) the body composition in different parts of the body. The system can be built by using a number of actuators as transmitters and receivers including sound, or in general a pressure wave. The receiver 16 might be for instance a microphone or pressure detector.

The proposed system presents a number of applications including monitoring of patients at intensive care units (ICUs) and general wards in hospitals, and elderly people in senior living facilities or at home. Determining the body composition of patients is of key importance, and at present there is not a sufficiently robust or accurate way of performing the required measurements. In ICUs, nurses have to write down the amount of liquid that a patient drinks and releases. This is not a user-friendly task and extremely imprecise as it does not take into account additional effects such as sweating. In nursing homes, elderly sometimes forget to drink leading to health risks. In this setting, determining the amount of water in the body can be used to help trigger alarms. Another application is the optimization of current systems running on body-fat weighing scales. Current weighing scales allow the user to determine their weight but also other parameters such as water or body-fat percentage. The system can also be applied to determine the structure of bones. Still another application refers to early detection of injures during normal activity such as walking or sports. The use of the proposed system can make those systems much more precise.

The invention claimed is:

1. A body wearable system for facilitating analysis related to a body of a user, the system comprising:
a first transducer configured to be placed at a first body location on the body of the user and to transmit a signal through at least a portion of the body of the user from the first body location;
a second transducer configured to be placed at a second body location on the body of the user, to receive the signal at the second body location via at least the portion of the body of the user, and to transmit the signal received at the second body location to one or more processors of the body wearable system;
a third transducer configured to be placed at a third body location on the body of the user between the first body location and the second body location, to receive the signal at the third body location, to generate a verification signal based the signal received at the third body location, and to transmit the verification signal to the one or more processors; and
the one or more processors configured to:
receive, from the second transducer, the signal received at the second body location;
receive the verification signal from the third transducer;
generate, at a first time, a first transfer function from the received signal, the first transfer function defining values at different frequencies for a predetermined signal parameters;
generate, at a second time, a further transfer function from the received signal;
compare the first transfer function with the further transfer function for the predetermined signal parameter and further adapt the comparison based on the received verification signal;
provide, via a display device, an output related to a preset threshold responsive to the adapted comparison indicating that a difference between the first transfer function and further transfer function exceeds the preset threshold.

2. A system according to claim 1, wherein the one or more processors generate, at the first time, a first transfer function corresponding to a wave velocity of the received signal and generate, at the second time, a further transfer function corresponding to the wave velocity of the received signal, wherein the adopted comparison indicates a delay of the received signal, and wherein the delay is indicative of a water content of the body of the user.

3. A system according to claim 1, wherein the predetermined parameter is an amplitude of the received signal and wherein the adopted comparison indicates an attenuation at the different frequencies of the amplitude of the received signal.

4. A system according to claim 1, wherein the predetermined signal parameter is one or more of a group velocity, a phase velocity, or a dispersion of the received signal.

5. A system according to claim 1 wherein the first transducer and the second transducer are synchronized.

6. A system according to claim 1, wherein the first transducer is configured to generate the signal using multiple different transmission technologies, the multiple different transmission technologies comprising body-coupled communication (BCC) and body-sound communication (BSC).

7. A system according to claim 1, wherein the second transducer comprises a microphone.

8. A system according to claim 1, wherein the body wearable system comprises a bracelet.

9. A method for facilitating analysis related to a body of a user, with a body wearable system comprising a first transducer configured to be placed at a first body location on the body of the user, a second transducer configured to be placed at a second body location on the body of the user, a third transducer configured to be placed at a third body location on the body of the user between the first body location and the second body location, and one or more processors, the method comprising:
- transmitting, with the first transducer, a signal through at least a portion of the body of the user from the first body location;
- receiving, with the second transducer, the signal at the second body location via at least the portion of the body of the user;
- transmitting, with the second transducer, the signal received at the second body location to the one or more processors of the body wearable system;
- receiving, with the third transducer, the signal at the third body location;
- generating, with the third transducer, a verification signal based the signal received at the third body location;
- transmitting, with the third transducer, the verification signal to the one or more processors;
- receiving with the one or more processors, from the second transducer, the signal received at the second body location;
- receiving, with the one or more processors, the verification signal from the third transducer;
- generating, with the one or more processors at a first time, a first transfer function from the received signal, the first transfer function defining values at different frequencies for a predetermined signal parameter;
- generating, with the one or more processors at a second time, a further transfer function from the received signal;
- comparing, with the one or more processors, the first transfer function with the further transfer function for the predetermined signal parameter and further adapting the comparison based on the received verification signal;
- providing, via a display device, an output related to a preset threshold responsive to the adapted comparison indicating that a difference between the first transfer function and the further transfer function exceeds the preset threshold.

10. A method according to claim 9, wherein the first transfer function corresponds to a wave velocity of the received signal and the further transfer function corresponds to the wave velocity of the received signal, wherein the adopted comparison indicates a delay of the received signal, and wherein the delay is indicative of a water content of the body of the user.

11. A method according to claim 9, wherein the predetermined parameter is an amplitude of the received signal and wherein the adopted comparison indicates an attenuation at the different frequencies of the amplitude of the received signal.

12. A method according to claim 9, wherein transmitting the signal comprises generating, with the first transducer, the signal using multiple different transmission technologies, the multiple different transmission technologies comprising body-coupled communication (BCC) and body-sound communication (BSC).

13. A method according to claim 9, further comprising synchronizing the first transducer and the second transducer.

14. A method according to claim 9, wherein the predetermined signal parameter is one or more of a group velocity, a phase velocity, or a dispersion of the received signal.

15. A method according to claim 9, wherein the body wearable system comprises a bracelet.

* * * * *